(12) United States Patent
Murray

(10) Patent No.: US 8,435,545 B2
(45) Date of Patent: *May 7, 2013

(54) CAPSULE HAVING BROAD COLOR SPECTRUM

(75) Inventor: Cale E. Murray, Browns Summit, NC (US)

(73) Assignee: Qualicaps, Inc., Whitsett, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/223,540

(22) Filed: Sep. 1, 2011

(65) Prior Publication Data

US 2013/0058989 A1    Mar. 7, 2013

(51) Int. Cl.
*A61K 9/00* (2006.01)
*A61K 9/44* (2006.01)

(52) U.S. Cl.
USPC .......................................... 424/400; 424/10.2

(58) Field of Classification Search .................... 424/400
See application file for complete search history.

(56) References Cited

U.S. PATENT DOCUMENTS

| | | | |
|---|---|---|---|
| 4,613,496 A | 9/1986 | Kopf et al. |
| 4,693,892 A | 9/1987 | Hegasy et al. |
| 6,517,865 B2 | 2/2003 | Cade et al. |
| 6,649,180 B1 | 11/2003 | Matsuura et al. |
| 6,887,307 B1 | 5/2005 | Scott et al. |
| 7,267,718 B2 | 9/2007 | Scott et al. |
| 7,429,619 B2 | 9/2008 | Kamath |
| 7,972,317 B2 | 7/2011 | Christon et al. |
| 2001/0024678 A1 | 9/2001 | Scott et al. |
| 2002/0187190 A1 | 12/2002 | Cade et al. |
| 2003/0070584 A1 | 4/2003 | Gulian et al. |
| 2003/0072729 A1 | 4/2003 | Szymczak et al. |
| 2003/0072731 A1 | 4/2003 | Gulian et al. |
| 2003/0108599 A1 | 6/2003 | Takubo et al. |
| 2003/0108607 A1 | 6/2003 | Szymczak |
| 2003/0211146 A1 | 11/2003 | Scott et al. |
| 2004/0022851 A1 | 2/2004 | Davis et al. |
| 2004/0105835 A1 | 6/2004 | Scott et al. |
| 2004/0228802 A1 | 11/2004 | Chang et al. |
| 2005/0249676 A1 | 11/2005 | Scott et al. |
| 2005/0265938 A1 | 12/2005 | Cohen et al. |
| 2006/0110327 A1 | 5/2006 | Emigh et al. |
| 2006/0177380 A1 | 8/2006 | Emigh et al. |
| 2007/0087939 A1 | 4/2007 | Cade et al. |
| 2007/0254024 A1 | 11/2007 | Cade et al. |
| 2008/0057118 A1 | 3/2008 | Alagarsamy et al. |
| 2008/0152595 A1 | 6/2008 | Emigh et al. |
| 2008/0175902 A1 | 7/2008 | Zajicek |
| 2008/0274187 A1 | 11/2008 | Cao |
| 2009/0004413 A1 | 1/2009 | Wagner et al. |
| 2009/0030091 A1 | 1/2009 | Shiraishi et al. |
| 2009/0234002 A1* | 9/2009 | Mickle et al. ................. 514/483 |
| 2010/0233252 A1 | 9/2010 | Tochio et al. |
| 2010/0330179 A1 | 12/2010 | Ault et al. |

FOREIGN PATENT DOCUMENTS

| | | |
|---|---|---|
| EP | 0221277 A2 | 5/1987 |
| WO | WO 2004080191 A1 * | 9/2004 |
| WO | WO 2006120227 A1 * | 11/2006 |
| WO | WO 2008134071 A1 * | 11/2008 |

OTHER PUBLICATIONS

X-rite. "A good guide to understanding color communication". http://www.xrite.com/documents/literature/en/L10-001__Understand__Color__en.pdf, accessed Nov. 2, 2012.*
Trescot et al. (2008). "Opioid Pharmacology". Pain Physician 2008: Opioid Special Issue, 11: S133-S153.*
Emerald Performance Materials, Technical Data, FD&C Red No. 40, Product Code 21DA6056, date unknown, pp. 1-2, Emerald Hilton Davis, LLC, Cincinnati, OH, US.
Emerald Performance Materials, Technical Data, FD&C Yellow No. 5 Powder, Product Code 21DA4400, date unknown, pp. 1-2, Emerald Hilton Davis, LLC, Cincinnati, OH, US.
Emerald Performance Materials, Technical Data, FD&C Yellow No. 6 Fine Powder, Product Code 21AA4415, date unknown, pp. 1-2, Emerald Hilton Davis, LLC, Cincinnati, OH, US.
Sangtae Kim, New Drug Development Timeline for USA, date unknown, Scientific, Parke Davis Pharmaceutical Research.
"List of Colors Permitted to be Used in Drugs in India—Rule 127 of the Drugs and Cosmetics Act 1945 and Rules 1945," date unknown, Ideal Cures Pvt. Ltd., Instacoat™ Film Coating Systems.
Murray et al., U.S. Appl. No. 13/274,703, filed Oct. 17, 2011.
Rockwood Pigments, Product Data, Ferroxide® Black 78P, Pigment Black 11, Color Index No. 77499, CAS 1317-65-9, copyright Aug. 2009.
Rockwood Pigments, Product Data, Ferroxide® Red 226P, Pigment Red 101, Color Index No. 77491, CAS 1309-37-1, copyright Aug. 2009.
Rockwood Pigments, Product Data, Ferroxide® Yellow 510P, Pigment Yellow 42, Color Index No. 77492, CAS 51274-00-1, copyright Aug. 2009.
"Sunset Yellow FCF," copyright Jul. 2011, Wikipedia, web site, pp. 1-3, http://en.wikipedia.org/wiki/Sunset__Yellow__FCF.
"Tartrazine," copyright Jul. 2011, Wikipedia, web site, pp. 1-5, http://en.wikipedia.org/wiki/Tartrazine.
"Allura Red AC," copyright Jul. 2011, Wikipedia, web site, pp. 1-4, http://en.wikipedia.org/wiki/Allura__Red__AC.
"Brilliant Blue FCF," copyright Jul. 2011, Wikipedia, web site, http://en.wikipedia.org/wiki/Brilliant__Blue__FCF.
CFR—Code of Federal Regulations Title 21, Part 73, Subpart A, Sec. 73.575 Titanium dioxide, copyright Jul. 2011, pp. 1-2.
CFR—Code of Federal Regulations Title 21, Part 73, Subpart B, Sec. 73.1575 Titanium dioxide, copyright Jul. 2011, pp. 1-2.

(Continued)

*Primary Examiner* — Robert T Crow
*Assistant Examiner* — Doan Phan
(74) *Attorney, Agent, or Firm* — Smith Moore Leatherwood LLP; Philip P. McCann

(57) ABSTRACT

The present invention is directed to a capsule comprising a water-soluble compound suitable for the capsule, and a mixture of colorant agents, wherein the color of the capsule may be in the range of 15<L<90; −30<a<+75; −37<b<+46 as measured in accordance with the Lab color space. The present invention further includes capsules containing a filling such as food, medicine, cosmetics, agrichemicals, feed or active biological ingredient.

20 Claims, No Drawings

OTHER PUBLICATIONS

"D&C Red No. 27 [CASRN 13473-26-2], D&C Red No. 28 [CASRN 18472-87-2]," copyright Oct. 2000.
Emerald Performance Materials, Technical Data, D&C Red 22 (Eosine Y.S., Purified), Product Code 25DA0050, date unknown, pp. 1-2, Emerald Hilton Davis, LLC, Cincinnati, OH, US, Aug. 19, 2004.
Emerald Performance Materials, Technical Data, D&C Red 28 (Phloxine B, Purified), Product Code 25DA0906, date unknown, pp. 1-2, Emerald Hilton Davis, LLC, Cincinnati, OH, US, Aug. 19, 2004.
Emerald Performance Materials, Technical Data, D&C Red 33, Product Code 25DA3733, date unknown, pp. 1-2, Emerald Hilton Davis, LLC, Cincinnati, OH, US, Aug. 19, 2004.
Emerald Performance Materials, Technical Data, D&C Yellow No. 10, Product Code 25DA3060, date unknown, pp. 1-2, Emerald Hilton Davis, LLC, Cincinnati, OH, US, Aug. 16, 2006.
Emerald Performance Materials, Technical Data, FD&C Blue No. 1 Powder, Product Code 21DA2204, date unknown, pp. 1-2, Emerald Hilton Davis, LLC, Cincinnati, OH, US, Oct. 13, 2004.
Emerald Performance Materials, Technical Data, FD&C Blue No. 2, Product Code 21DA2242, date unknown, pp. 1-2, Emerald Hilton Davis, LLC, Cincinnati, OH, US, Sep. 13, 2004.
Emerald Performance Materials, Technical Data, FD&C Green No. 3, Product Code 21DA4203, date unknown, pp. 1-2, Emerald Hilton Davis, LLC, Cincinnati, OH, US, Oct. 13, 2004.
Emerald Performance Materials, Technical Data, FD&C Red No. 3, Product Code 21DA6009, date unknown, pp. 1-2, Emerald Hilton Davis, LLC, Cincinnati, OH, US, Oct. 13, 2004.
Invitation to Pay Additional fees and, Where Applicable, Protest Fee, mailed on Dec. 10, 2012 in PCT/US2012/052998.

* cited by examiner

CAPSULE HAVING BROAD COLOR SPECTRUM

FIELD OF THE INVENTION

The present invention relates to capsules, and particularly a capsule comprising a mixture of colorants, which provides the capsule with a broad color spectrum as set forth by the Hunter Lab color space.

BACKGROUND

A wide variety of capsules are known including gelatin capsules such as soft capsules prepared by adding glycerin to gelatin, gelatin hard capsules which are essentially composed of gelatin and do not contain glycerin, cellulose-based hard capsules which are essentially composed of a cellulose derivative substrate, and the like. Hard capsules are commonly used in the pharmaceutical and health food fields. Of the hard capsules, gelatin capsules are most widely used. They are formed from a film of a composition comprising gelatin as a base, and other elements including opacifying agent, colorant agent, pigment, and other additives. Typically, gelatin capsules are manufactured by dipping pins in an aqueous gelatin solution having the above components blended, drawing out the pins with the aqueous gelatin solution adhering to the pins, and drying the gelatin coats.

Such capsules include various colorants to provide a color of the capsule and printing on the capsule resulting from edible inks imprinted on the surface of the capsule.

A capsule according to the invention will have a shelf life of no less than sixty months, which may be the future expiry date of capsules. In this case, shelf life may be determined as regards the stability of the shell when monitoring attributes of the capsule including moisture content, weight, brittleness, and overall physical appearance of the capsule. These attributes will be stable for empty hard gelatin capsules stored in a properly sealed container at the manufacturer's stated storage conditions. For example, for a capsule having a shelf life of at least sixty months, the shell of the capsule will not fail storage stability tests due to weight variation for a storage period of at least sixty months.

Such capsules may include an active biological ingredient such as pharmaceuticals, and hence, be subject to FDA testing and approval. Testing of such capsules often requires a 3 month accelerated condition storage testing of the capsule filled with active biological ingredient(s) and any excipient(s) for evaluation of any issues related to interaction of the capsule components, colorants or edible inks with the filled materials. The completion of this testing may take over 6 months.

To achieve testing with the assurance that the colorant and edible ink utilized for the capsules encompasses the commercial trade dress, this testing is typically completed after color and print selection. The color and print selection process and subsequent custom capsule manufacturing process may require 6 months or more prior to completion, which results in a 6 month delay in the approval of the pharmaceutical capsule. Any delay in the approval process is costly and unwanted. Discoloration of the shell would be considered a minor issue and there is no extended benefit from this product in that regard. The major focus of stability studies is potency and availability of the active ingredient. The customer's main concern related to capsules during their stability evaluation is that the capsule ingredients do not interact with their fill material causing an issue with potency or availability.

The present invention is directed to a capsule, which includes a mixture of colorants, which provides color of the capsule within an acceptable range for FDA testing purposes.

SUMMARY

The present invention is directed to a capsule comprising
  a) a water-soluble compound suitable for the capsule, and
  b) a mixture of colorant agents,
wherein the color of the capsule may be in the range of $15<L<90$; $-30<a<+75$; $-37<b<+46$ as measured by in accordance with the Lab color space.

Another embodiment of the invention is directed to a capsule comprising
  a) a water-soluble compound suitable for the capsule,
  b) a mixture of colorant agents comprising iron oxide yellow, iron oxide black, iron oxide red, titanium dioxide, FD&C Blue No 1, FD&C Blue No 2, FD&C Yellow No 6, FD&C Yellow No 5, FD&C Red No 40, FD&C Red No 3, D&C Red No 22, D&C Red No 33, D&C Red No 28, FD&C Green No 3, and D&C Yellow No 10; and
  c) an edible ink imprinted on the capsule.

Another embodiment of the invention is directed to a capsule comprising
  a) a water-soluble compound suitable for the capsule,
  b) a mixture of colorant agents comprising colors E172(i), E172(ii), E172(iii), E171, E133, E110, E131, E123, E122, E150, E120, E124, E140, E129, E127, E132, E102 and E151, and
  c) an edible ink imprinted on the capsule.

Numerous other features and advantages of the present invention will appear from the following description.

DETAILED DESCRIPTION

While typical aspects of embodiment and/or embodiments have been set forth for the purpose of illustration, this Detailed Description should not be deemed to be a limitation on the scope of the invention. Accordingly, various modifications, adaptations, and alternatives may occur to one skilled in the art without departing from the spirit and scope of the present invention. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, the term "about" modifying the quantity of an ingredient in the compositions of the invention refers to variation in the numerical quantity that can occur, for example, through typical measuring and liquid handling procedures; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture.

The term 'color' as referred to herein include any primary color, i.e., white, black, red, blue, violet, orange, yellow, green, and indigo as well as any declination thereof or mixture thereof.

The term "Lab color space" is a color-opponent space with dimension L for lightness, and a and b for the color-opponent dimensions, based on nonlinearly compressed CIE XYZ color space coordinates.

The term "C.I." as used herein mean a prefix for a listing of colorants listed according to Color Index Generic Names and Color Index Constitution Numbers as established by the Color Index International (CIE) which is a reference database jointly maintained by the Society of Dyers and Colourists and the American Association of Textile Chemists and Colorists.

The term "E numbers", such as E120 etc, are number codes for food colorant additives that have been assessed for use within the European Union (the "E" prefix stands for "Europe").

The term "edible ink" as used herein refers to any composition that is suitable for human consumption and forms an image layer on an edible or inedible substrate in a commercially feasible time. Edible inks suitable for human consumption comply with applicable standards such as FD&C regulations in the United States and E.E.C. standards in the European Union.

The term "opacity" as used herein refers to the degree to which a film obscures a material or substrate beneath it.

The term "% by weight", "wt %" or "% wt" as used herein and referring to components of the capsule, is to be interpreted as based on the weight of the water-soluble compound, often based on gelatin.

These terms may be defined with additional language in the remaining portions of the specification.

The present invention is directed to a capsule comprising
a) a water-soluble compound suitable for the capsule, and
b) a mixture of colorant agents,
wherein the color of the capsule may be in the range of $15<L<90$; $-30<a<+75$; $-37<b<+46$ as measured by in accordance with the Lab color space.

Another embodiment of the invention is directed to a capsule comprising
a) a water-soluble compound suitable for the capsule,
b) a mixture of colorant agents comprising iron oxide yellow, iron oxide black, iron oxide red, titanium dioxide, FD&C Blue No 1, FD&C Yellow No 6, FD&C Red No 40, D&C Red No 28, FD&C Blue No 2, FD&C Yellow No 5, FD&C Red No 40, FD&C Red No 3, D&C Red No 22, D&C Red No 33, D&C Red No 28, FD&C Green No 3, and D&C Yellow No 10; and
c) an edible ink imprinted on the capsule.

Another embodiment of the invention is directed to a capsule comprising
a) a water-soluble compound suitable for the capsule,
b) a mixture of colorant agents comprising colors E172(i), E172(ii), E172(iii), E171, E133, E110, E131, E123, E122, E150, E120, E124, E140, E129, E127, E132, E102 and E151, and
c) an edible ink imprinted on the capsule.

As used herein, the term capsule generally refers to capsules as used to include a filing including food, medicine, cosmetics, agrichemical, feed, or an active biological ingredient. In particular, such capsules may be used in the manufacture of pharmaceuticals, wherein active ingredients such as medicines are enclosed in a relatively stable shell known as a capsule, allowing them to, for example, be taken orally.

The two main types of capsules are hard-shelled capsules, generally referred to as hard capsules and soft-shelled capsules, generally referred to as soft capsule. Hard capsules are normally used for dry, powdered ingredients or miniature pellets or tablets whereas soft capsules are primarily used for oils and for active ingredients that are dissolved or suspended in oil. The hard capsules may be a two part capsule including a body and a cap.

Capsules may generally comprise a water-soluble compound, a mixture of colorants, opacifying agents; flavoring agents and edible ink(s) imprinted on the surface of the capsule. In particular, a hard capsule comprises a water-soluble compound as a principal component. The water-soluble compound may be selected from a gelatin or cellulose compound.

The water-soluble compound may include an animal protein mainly gelatin, or a plant polysaccharide or their derivatives like carrageenans and modified forms of starch and cellulose. Hard capsules made with gelatin, generally include about 80 wt % of gelatin and 15% water. In one embodiment, the water-soluble compound may be hydroxypropyl methyl cellulose (HPMC) which is used to make a capsule. HPMC is specified in the Pharmacopoeia of Japan. In the capsule shell application, it is recommended to use the pharmacopoeia-specified products. For HPMC, the Pharmacopoeia specifies three types, hydroxypropyl methyl cellulose 2208, hydroxypropyl methyl cellulose 2906, and hydroxypropyl methyl cellulose 2910, depending on the contents of MO groups. It is specified that hydroxypropyl methyl cellulose 2208 contains about 19 to about 24% wt of MO groups and about 4 to about 12% wt of HPO groups in a total of about 23 to about 36% wt; hydroxypropyl methyl cellulose 2906 contains about 27 to about 30% wt of MO groups and about 4 to about 7.5% wt of HPO groups in a total of about 31 to about 37.5% wt, and hydroxypropyl methyl cellulose 2910 contains about 28 to about 30% wt of MO groups and about 7 to about 12% wt of HPO groups in a total of about 35 to about 42% wt. Any of these celluloses may be used in the practice of the invention as long as the total content of MO and HPO groups is up to about 37.6% wt. Also acceptable are mixtures in which any two or more of these celluloses are mixed to adjust the total content of MO and HPO groups to that range.

A gelling agent, when used, may be selected from among, for example, carrageenan, tamarind seed polysaccharide, pectin, curdlan, furcellaran, gellan gum, and mixtures thereof. Of these, carrageenan is especially preferred because it has a high gel strength and exhibits good gelling properties in the co-presence of a specific ion so that it may achieve effective gelation even when added in small amounts. While there are known three types: kappa-carrageenan or iota-carrageenan and lambda-carrageenan, kappa-carrageenan and/or iota-carrageenan are preferred.

The amount of the gelling agent when used is not critical and may be suitably determined in accordance with the type of cellulose ether and gelling agent, the intended application of film, and film forming method.

As the gelling aid used herein, any substance that can promote gelation by the gelling agent may be employed. Depending on the type of the gelling agent, the gelling aid may be selected from a potassium ion, calcium ion, ammonium ion, and various organic compounds which can promote gelation by the gelling agent. Especially when capsule shells are formed using carrageenan as the gelling agent, a potassium ion or calcium ion or both are preferably used. The potassium ion may be blended in the form of its water-soluble compound such as potassium chloride, potassium phosphate or potassium citrate. The calcium ion may be blended in the form of its water-soluble compound such as calcium chloride.

Like the gelling agent, the amount of the gelling aid used is not critical and may be suitably determined in accordance with the type of water-soluble compound and gelling agent, the intended application of film, and film forming method. When capsule shells are formed by the well-known dipping method, for example, it is recommended to use about 0.05 to 25 parts by weight and especially about 0.25 to 15 parts by weight, calculated as ion, of the gelling aid per 100 parts by weight of the cellulose ether. Less than 0.05 part of the gelling aid may promote gelation of the gelling agent to a less extent and fail to produce a film of a sufficient thickness to enable shell formation by the dipping method. More than 25 parts by weight of the gelling aid may form a gel in a dipping solution for rendering it difficult to form a film, and in addition, adversely affect the disintegration (i.e., dissolution after administration) of the resulting film, which is inconvenient as the capsule shells.

Additionally, the capsule shell material may contain 0 to 10% wt pharmaceutically acceptable lubricants based upon the weight of the hydrophilic polymer. The lubricant may be selected from aluminum stearate, calcium stearate, magnesium stearate, tin stearate, talc, sodium lauryl sulfate, lecithins, mineral oils, stearic acid or silicones or mixtures thereof. The capsules of the present invention may include from about 0.1% wt to about 0.2% wt of sodium lauryl sulfate for gelatin capsules.

In addition, the capsule may include up to about 0.2 wt % of carboxymethylcellulose, up to about 0.2 wt % of acetic acid, and up to about 0.6 wt % of silicon dioxide.

The capsule of the present invention includes a mixture of colorants that allows the color of the capsule may be in the range of $15<L<90$; $-30<a<+75$; $-37<b<+46$ as measured by in accordance with the Lab color space. One embodiment includes a mixture of colorants comprising iron oxide yellow, iron oxide black, iron oxide red, titanium dioxide, FD&C Blue No 1, FD&C Yellow No 6, FD&C Red No 40, D&C Red No 28, FD&C Blue No 2, FD&C Yellow No 5, FD&C Red No 3, D&C Red No 22, D&C Red No 33, D&C Red No 28, FD&C Green No 3, and D&C Yellow No 10.

Another embodiment includes a mixture of colorants comprising colors E172(i), E172(ii), E172(iii), E171, E133, E110, E131, E123, E122, E150, E120, E124, E140, E129, E127, E132, E102, and E151.

The Lab color space and colorants are further defined as follows. The color scale values, utilized herein to define the darkness/lightness of the materials of the absorbent articles according to the present invention, are the widely accepted Hunter LAB scale. Measurements are made with a Hunter Color spectrocolorimeter. A Lab color space as described by Hunter's L, a, and b, is a color-opponent space with dimension L for lightness and a and b for the color-opponent dimensions, based on nonlinearly compressed CIE XYZ color space coordinates.

In general, Hunter Color "L" scale values are units of light reflectance measurement, and the higher the value is, the lighter the color is since a lighter colored material reflects more light. Generally, "L" denotes the level of white/black, or lightness, and the "a" and "b" values are termed the opponent color axes. The "a" opponent color axis represents, approximately, the redness or greenness (positive or negative) while the "b" opponent color axis represents the yellowness or blueness (positive or negative). In particular, in the Hunter Color system the "L" scale contains 100 equal units of division. Absolute black is at the bottom of the scale (L=0) and absolute white is at the top of the scale (L=100). The color gray can be represented by "L" values between 0 and 100 at a and b values of zero.

The color red can be represented by a positive "a" value while the color green can be represented by a negative "a" value. The color yellow can be represented by a positive "b" value while the color blue can be represented by a negative "b" value. All values included and there between for each of the colors associated with the Hunter values are within the scope of the embodiments of this invention and can be represented as red, green, blue, yellow, purple, tan, brown, beige, black, white, gray, orange, pink, lavender, pink and combinations and mixtures thereof based on their particular Hunter Lab values.

Lab Color Test

Color-containing solutions which may be utilized to manufacture capsules may be tested in a liquid state and at an elevated temperature and moisture level to provide the most accurate means of presenting the color sample to the instrument. Reflectance color is measured using the Hunter Lab LABSCAN® XE spectrocolorimeter obtained from Hunter Associates Laboratory of Reston, Va. The spectrophotometer is set to the Hunter Lab color scale and with a D65 illumination. The Observer is set at 10°. The Mode is set at 45/0°. Area View is set to 1.75". Port Size is set to 2.00" for all materials. The spectrocolorimeter is standardized prior to sample analysis utilizing the black and white reference tiles supplied from the vendor with the instrument. Standardization is done according to the manufacturer's instructions as set forth in the Hunter Lab EasyMatch® QC Manual, Manual Version 1.1, October 2004, A60-1012-402.

If cleaning is required of the reference tiles or samples, tissues that do not contain embossing, lotion, or brighteners should be used; a suitable tissue is KIMWIPES® Delicate Task Wipers. Any sample point on the externally visible surface of the element containing the imparted color to be analyzed should be selected. Sample points are selected so as to be close in perceived color. A sample of the material being tested is placed over the spectrocolorimeter's sample port. The sample comprising the color to be analyzed must be larger than the sample port to ensure accurate measurements. A white tile, as supplied by the manufacturer, is placed behind the externally visible surface. The L, a, and b values are read and recorded. A minimum of five readings are obtained for the externally visible surface. The readings are averaged to yield the reported L, a, and b values for a specified color on an externally visible surface of an element.

The capsule of the present invention includes a mixture of colorants that allows the color of the solution to be in the range of $15<L<90$; $-30<a<+75$; and $-37<b<+46$.

The colorants used in the mixture of colorants are further described as follows and include any appropriate lake versions of these colorants. Lake versions, generally referred to as lakes, are made by combining dyes with salts to make insoluble compounds. Lakes are known to be more stable than dyes and are ideal for coloring products containing fats and oils or items lacking sufficient moisture to dissolve dyes. The colorants listed herein will include the lakes version.

Colorants and mixtures of colorants used in the present invention are generally determined by a number of steps including review of the FDA guidelines for colorants acceptable for use in oral dose drug products, a review of the specifications for those products, a review of the potential application of those products in capsule manufacturing operations, a review of the coloring potential for those products, and a review of current and historical color formulations. The initial list of colorants may include all colorants approved for use in oral dose drugs in the United States as of January 2011 for example. Technical specifications for these colorants were reviewed. Any colorant which has properties which were not compatible (i.e. solubility, microbial purity) or are difficult to use with manufacturing processes or do not add value to coloring the capsule are not used.

Selection of colorants also involves what is called opacity which is used to mask the ingredients, fill volume, fill color, or other attributes is an important component to capsule color selection. Each of the colorants will contribute varying levels of opacity to a capsule. Soluble dyes, such as D&C Yellow No 10, contribute virtually no opacity to a capsule even at the maximum usage limits. Pigments such as titanium dioxide contribute a large amount of opacity to a capsule even in amounts much lower than the maximum usage limits.

The following is a list of colorants suitable for the present invention. It is noted that the list of colorants may vary from country to country due to regulations.

Iron oxide yellow, E172(iii), is also known as the monohydrate (FeO(OH))).H$_2$O or otherwise described as iron(III) hydroxide Fe(OH)$_3$; other names include IOY (as used in the examples herein), yellow iron oxide, and ferric oxide yellow.

Iron oxide black, E172(i), is also known by the IUPAC name iron(II) diiron(III) oxide. Iron(II,III) oxide is the chemical compound with formula Fe$_3$O$_4$ wherein iron oxide black generally includes more than 95% Fe$_3$O$_4$; other names ferrous ferric oxide, ferroso ferric oxide, iron(II,III) oxide, magnetite, IOB (as used in the examples herein), black iron oxide, and lodestone.

Iron oxide red, E172(ii), is also known by its formula Fe$_2$O$_3$ and also known as ferric oxide, hematite, ferric iron, iron(III) oxide or ferric oxide, synthetic maghemite, colcothar, IOR (as used in the examples herein), iron sesquioxide, and CI No 77491.

Titanium dioxide, also known as titanium(IV) oxide or titania, is the naturally occurring oxide of titanium; chemical formula TiO$_2$, which is used in the examples herein. Other names include titania, rutile, anatase, brookite, Pigment White 6, CI-77891 and E171

FD&C Blue No 1 and its lakes, is also known as Brilliant Blue FCF, E133, CI-42090, Acid Blue 9, D&C Blue No. 4, B1 (as used in the examples herein), Alzen Food Blue No. 1 Atracid Blue FG, Erioglaucine, Eriosky blue, Patent Blue AR, and Xylene Blue VSG. The IUPAC name for FD&C Blue No. 1 is ethyl-[4-[[4-[ethyl-[(3-sulfophenyl) methyl]amino]phenyl]-(2-sulfophenyl)methylidene]-1-cyclohexa-2,5-dienylidene]-[(3-sulfophenyl)methyl]azanium.

FD&C Yellow No 6 and its lakes, is a synthetic yellow azo dye. Other names of FD&C Yellow No 6 include, but are not limited to Sunset Yellow FCF, Y6 (as used in the examples herein), Orange Yellow S, C.I. 15985, or E110. The IUPAC name for FD&C Yellow No. 6 is disodium 6-hydroxy-5-[(4-sulfophenyl)azo]-2-naphthalenesulfononate.

FD&C Red No 40 and its lakes, is a red azo dye that goes by several names including Allura Red AC, Allura Red, Food Red 17, C.I. 16035, FD&C Red 40, R40 (as used in the examples herein), E129, and the IUPAC name is 2-naphthalenesulfonic acid, 6-hydroxy-5-((2-methoxy-5-methyl-4-sulfophenyl)azo)-, disodium salt, and disodium 6-hydroxy-5-((2-methoxy-5-methyl-4-sulfophenyl)azo)-2-naphthalenesulfonate.

D&C Red No 28 and its lakes, is also known as Acid Red 92, Cyanosin; Cyanosine; Eosine bluish; Eosine Blue; Cyanosin B; R28 (as used in the examples herein), Eosin Blue; Phloxine P; Phloxin B; Eosine I Bluish; Acid red 92; C.I. 45410 and the IUPAC name is Disodium 2',4',5',7'-tetrabromo-4,5,6,7-tetrachloro-3-oxospiro[2-benzofuran-1,9'-xanthene]-3',6'-diolate.

D&C Yellow No 10 and its lakes, is also known as Quinoline yellow, Quinoline Yellow WS, C.I. 47005, or Food Yellow 13, is a yellow food dye. Other names include Food Yellow 13, D&C Yellow No. 10, Y10 (as used in the examples herein), Acid yellow 3, Quinidine Yellow KT, Japan Yellow 203, Lemon Yellow ZN 3, C.I. 47005 and the IUPAC name is Sodium 2-(1,3-dioxoindan-2-yl)quinolinedisulfonate.

FD&C Blue No. 2 and its lakes, an indigotine Indigo dye is an organic compound with a distinctive blue color of dark blue, is also known as indigo carmine as well as the common chemical name 2,2'-Bis(2,3-dihydro-3-oxoindolyliden), and names of E132, B2 (as used in the examples herein), and Food Blue 1.

FD&C Green No. 3 and its lakes, is also known as Fast Green FCF, Food green 3, Green 1724, Solid Green FCF, G3 (as used in the examples herein), E143, and C.I. 42053, is a sea green triarylmethane food dye. The IUPAC name for FD&C Green No. 3 is ethyl-[4-[[4-[ethyl-[(3-sulfophenyl) methyl]amino]phenyl]-(4-hydroxy-2-sulfophenyl) methylidene]-1-cyclohexa-2,5-dienylidene]-[(3-sulfophenyl)methyl]azanium.

FD&C Red No. 3 and its lakes, is also known as E127, R3 (as used in the examples herein), and Erythrosine, is an organoiodine compound. It is cherry-pink synthetic, primarily used for food coloring. It is the disodium salt of 2,4,5,7-tetraiodofluorescein. Its maximum absorbance is about 530 nm. It has the IUPAC name 2-(6-Hydroxy-2,4,5,7-tetraiodo-3-oxo-xanthen-9-yl)benzoic acid.

D&C Red 22 and its lakes, is also known as Red 22 and Acid Red 87 and is a disodium salt of 2,4,5,7-tetrabromofluorescein.

D&C Red 33 and its lakes, is a red azo dye that is also known as Acid Red 33, Red 33, Azo grenadine, Azo fuchsine, Acid fuchsine D, Redusol Z, Azo magenta G, Certicol Red B, Fast acid magenta, Hexylan Red B, Acetyl Red B, Naphthalene Red B, C.I. 17200, and has the IUPAC name Disodium 5-amino-4-hydroxy-3-(phenylazo)-naphthalene-2,7-disulfonate.

FD&C Yellow No. 5 and its lakes, is also known as food yellow 4, acid yellow 23, tartrazine, Y5 (as used in the examples herein), E102, C.I. 19140 and has the IUPAC name Trisodium (4E)-5-oxo-1-(4-sulfonatophenyl)-4-[(4-sulfonatophenyl)hydrazono]-3-pyrazolecarboxylate.

Color E131 and its lakes, is also known as Patent Blue, Patent Blue V Food Blue 5 or Sulphan Blue, is a dark bluish synthetic dye. It is a sodium or calcium salt of [4-(α-(4-diethylaminophenyl)-5-hydroxy-2,4-disulfophenylmethylidene)-2,5-cyclohexadien-1-ylidene]diethylammonium hydroxide inner salt.

Color E120 and its lakes, is also known as Cochineal Carminic Acid, Carmine, Crimson Lake, Cochineal, Natural Red #4, or C.I. 75470, is a pigment of a bright red color.

Color E122 and its lakes, is also known as Azorubine, carmoisine, Food Red 3, Azorubin S, Brillantcarmoisin O, Acid Red 14, or C.I. 14720. It usually comes as a disodium salt and is a red to maroon powder.

Color E123 and its lakes, is known as Amaranth, FD&C Red No. 2, C.I. Food Red 9, Acid Red 27, Azorubin S, or C.I. 16185, which is a dark red to purple azo dye. Its water solution has absorption maximum at about 520 nm. Amaranth is an anionic dye. The IUPAC name of E123 is trisodium (4E)-3-oxo-4-[(4-sulfonato-1-naphthyl)hydrazono]naphthalene-2,7-disulfonate.

Color E124 and its lakes, is also known as Ponceau 4R, C.I. 16255, Cochineal Red A, C.I. Acid Red 18, Brilliant Scarlet 3R, Brilliant Scarlet 4R, New Coccine, SX purple. The IUPAC name of Color 124 is trisodium (8Z)-7-oxo-8-[(4-sulfonatonaphthalen-1-yl)hydrazinylidene]naphthalene-1,3-disulfonate Color E140 and its lakes, is also known as S.C. Chlorophyllin and CI No 75810; Chlorophyll is registered as a food additive (colorant).

E150 is generally referred to as Caramel, and is also known as E150(a).

Color E151 and its lakes, is also known as Brilliant Black, Black PN, and Brilliant Black BN, which is a synthetic coal tar and azo dye. It has the appearance of solid, fine powder or granules and it is very soluble in water The following table provides a correlation of the names of listed colorants and the E numbers.

TABLE 1

| Common Name | E Number |
|---|---|
| Iron oxide yellow | E172(iii) |
| Iron oxide black | E172(i) |
| Iron oxide red | E172(ii) |
| Titanium Dioxide | E171 |
| FD&C Blue No 1 | E133 |
| FD&C Blue No 2 | E132 |
| FD&C Yellow No 6 | E110 |
| FD&C Yellow No 5 | E102 |
| FD&C Red No 40 | E129 |
| FD&C Red No 3 | E127 |
| D&C Red No 22 | — |
| D&C Red No 33 | — |
| D&C Red No 28 | |
| FD&C Green No 3 | E143 |
| D&C Yellow No 10 | |
| FD&C Red No 2 | E123 |
| Patent Blue V | E131 |
| Carmoisine | E122 |
| Caramel | E150 |
| Carmine | E120 |
| Ponceau 4R | E124 |
| S.C. Chlorophyllin | E140 |
| Black PN | E151 |

The amounts of colorant utilized in the mixture of colorants are generally dependent on various factors including the available colorant saturation of any gelatin solution used to make gelatin capsules, the solubility of those colorant(s), the coloring potential of those colorants, the opacity provided by those colorants, and the levels of those colorants listed in the FDA inactive ingredients guide as of January 2011 as set forth in the Inactive Ingredients Guide(IIG) list published by FDA, which lists levels of each colorant in products already approved by FDA.

A preferred maximum liquid mixture of colorant solution/suspension addition to gelatin solution is about 18 wt %. This 18 wt % represents a percentage of total color solution/suspension including the water utilized to solubilize the material when compared to the amount of gelatin solution. This percentage is not aligned with the maximum percentages reported for the individual colorants, which are measures of the individual colorant as a percentage of the overall capsule. Therefore, the 18 wt % was selected as the maximum amount of liquid colorant solution/suspension that would be added to gelatin solution for the invention.

Each of the colorants has a different level of water solubility/suspendability, so those levels were examined to determine which colorants gave the highest available concentration of colorant per milliliter of colorant solution/suspension. The higher the concentration of colorant in the solution/suspension, the lower the amount of volume that colorant would contribute to the overall 18 wt % limit while still giving adequate coloring ability.

Each of the colorants has a different level of coloring potential. Some colorants can be considered "weak", such that higher than average levels of colorant are required to achieve acceptable color shades. Conversely, some colorants can be considered as "strong", such that lower than average levels of colorant are required to achieve acceptable color shades. A "strong" color may be used in lower amounts which would contribute less to the overall 18 wt % limit, while a "weak" color will require use in higher amounts which will contribute more to the overall 18 wt % limit.

Exceeding these amounts in total results in a color which overstaturates the gelatin solution used to prepare hard gelatin capsules with colorant material. This oversaturation can result in poor gelatin film formation which can result in reduced capsule strength and material deformities.

TABLE 2

| Maximum Amounts of colorants | |
|---|---|
| Colorant | Maximum Amount (%) |
| FD&C Blue No. 1 | 0.23 |
| FD&C Blue No. 2 | 0.04 |
| D&C Yellow No. 10 | 0.09 |
| FD&C Yellow No. 5 | 0.23 |
| FD&C Yellow No. 6 | 0.09 |
| FD&C Red No. 3 | 0.23 |
| D&C Red No. 28 | 0.16 |
| FD&C Red No. 40 | 0.35 |
| FD&C Green No. 3 | 0.06 |
| D&C Red No. 22 | 0.12 |
| D&C Red No. 33 | 0.05 |
| Titanium Dioxide | 1.92 |
| Iron Oxide Yellow | 0.35 |
| Iron Oxide Red | 0.70 |
| Iron Oxide Black | 0.24 |

In particular, the capsule of the present invention comprises up to 0.35 wt % of iron oxide yellow, up to about 0.24 wt % of iron oxide black, up to about 0.70 wt % of iron oxide red, up to about 1.92 wt % of titanium dioxide, up to about 0.23 wt % of FD&C Blue No 1, up to about 0.04 wt % of FD&C Blue No. 2, up to about 0.09 wt % FD&C Yellow No 6, up to about 0.23 wt % of FD&C Yellow No. 5, up to about 0.35 wt % of FD&C Red No 40, up to about 0.23 wt % of FD&C Red No. 3; up to about 0.12 wt % of D&C Red No. 22; or up to about 0.05 wt % of D&C Red No. 33, up to about 0.16 wt % of D&C Red No 28, up to about 0.06 wt % of FD&C Green No. 3, and up to about 0.09 wt % of D&C Yellow No 10.

The capsule of the present invention may further comprise an edible ink. In particular the capsule may be imprinted with at least two edible inks Edible inks are commercially available from numerous sources including numerous ink suppliers who commonly supply edible inks for capsules for use in the pharmaceutical industry. In general, it has been found that about 90% of pharmaceutical capsules utilize either black or white edible ink for their primary imprinting of capsules wherein the black or white include colorants. The colorants used in the mixture of colorants and listed herein have extensive use in the coloring of edible inks, including the black and white edible inks selected for the invention. The colorants used in edible inks are included in the overall dosage form formulation, whether used to color the ink or the capsule.

The edible ink compositions vary greatly by manufacturer and color that the ink achieves. Edible ink includes Shellac from about 10% to about 30% by weight, about 20% to 70% by weight of at least one solvent, and at least one soluble or insoluble pigment from about 10 wt % to about 40 wt %. The shellac provides structure, enhances adherence to the printing plate and capsule, and acts as a pigment carrier. An edible ink formulation may include 10 wt % to about 30 wt % shellac.

The formulation of the edible ink also includes at least one solvent. Solvents provide solubility enhancements for the shellac and pigments, enhances adherence to the printing plate and capsule, regulate the rate at which the ink dries, and regulate the ink viscosity. Suitable solvents may include isopropyl alcohol, ethanol, water, butyl alcohol, propylene glycol, ammonium hydroxide, sodium hydroxide, povidone, simethicone, and potassium hydroxide. An edible ink formulation may include from about 10 wt % to about 30 wt % ethanol, from about 1 wt % to about 30 wt % isopropyl alcohol, from about 1 wt % to about 5 wt % butyl alcohol, from about 1 wt % to about 5 wt % propylene glycol, or from about 1 wt % to about 3 wt % ammonium hydroxide.

To provide a properly colored image, the edible ink includes one or more soluble or insoluble pigments. The pigments should be present in a sufficient concentration to consistent pigmentation as the ink is applied. An edible ink formulation may include from about 25 wt % to about 35 wt % pigment. The edible ink may have a specific gravity, referred to herein as the ink specific gravity, of from about 1.0 kg/l to about 1.3 kg/l at 25° C., or about 1.2 kg/l. The pigments used in the aqueous formulation of the edible ink may vary widely, and any known pigment approved for human consumption in a particular country may be used. Suitable pigments include, for example, Iron Oxides, Titanium Dioxide, and FD&C colorants such as Yellow No 5, Yellow No 6, Red No 3, Red No 40, Blue No 1, Blue No 2, the lake versions of any of these, and mixtures thereof.

The printing of the capsule of the present invention may be done using a common offset printing method using an imprinting machine as described as follows. A capsule is transferred to a holding cavity specifically sized for the capsule dimension to be imprinted. Multiple cavities are arranged linearly across the width of the imprinting machine as sections of metal plates (hereinafter referred to as a "cavity bar") used to transport capsules. The width of the cavity bar is determined by the practical width of the machine. A preferred cavity bar contains from 10-16 cavities. All cavities of a cavity bar are filled simultaneously. The cavity bar is then transported forward on the imprinting machine and the next cavity bar is filled with capsules.

A gravure roll is an engraved cylinder utilized for offset printing. A gravure roll may be engraved with a variety of characters and designs desirable for product identification. Engravings need not be identical for the capsule cap and body. The number of engravings across the gravure roll is identical to the number of cavities present on the cavity bar. The number of engravings around the gravure roll is dependent on whether the printing is to be applied across or around the capsule. If the print is to be applied across the capsule, then the gravure roll may contain as many as 14 engravings around the roll. If the print is to be applied around the capsule, then the gravure roll may contain as many as 7 engravings around the roll. The volume of the engraving is determined by the shape and depth of the engraving. The gravure roll is rotated at an appropriate speed to match the speed the cavity bars travel on the machine. This speed can be from about 0 to about 800 cavity bars per minute. The preferred speed is from about 400 cavity bars per minute to about 700 cavity bars per minute. The gravure roll is rotated to be submerged in a pan of the selected imprinting ink. As the gravure roll rotates, ink is applied to the face of the gravure roll and is also captured in the individual engravings. The excess ink present on the face of the gravure roll is then removed by a stationary mechanical scraper as the gravure roll rotates. This leaves the face of the gravure roll clean with no presence of ink, while the engravings hold a desired amount of ink. The gravure roll then contacts with a transfer roll which is counter rotating to the gravure roll. The transfer roll is typically manufactured from a pliable material such as a flexible polymer or rubber. After the ink is captured by the gravure roll engraving and the excess ink is removed by the mechanical scraper, the gravure roll contacts the transfer roll. In this contact, the ink from the gravure roll engraving is deposited on the transfer roll in the shape of the desired imprinting design. The cavity bars holding the capsules to be imprinted are moved below the transfer roll. The transfer roll lightly contacts the capsules as the cavity bar moves underneath the transfer roll. This contact, often referred to as "kiss" begins the transfer of ink from the transfer roll to the capsules. The transfer roll continues to rotate until the deposited ink is fully transferred to the capsules. Thus the design of the engraving of the gravure roll is deposited as ink onto the capsule. To imprint capsules with different inks on the cap and body, the imprinting machine design described above is extended to allow for the use of two gravure rolls and two transfer rolls, with one being used for each the cap and body. In either case, the ink adheres and dries to the capsule almost instantaneously. The capsules are then transported to a container for storage.

The capsule of the present invention was imprinted using two gravure rolls with designs engraved at a rate of 12 designs across the roll and 7 designs around the roll. The two gravure roll and two transfer roll setup described previously was utilized to achieve an approximately 1 mm wide printed band around the mid points of the cap and body of the capsule. The cap portion was imprinted with edible black ink while the body portion was imprinted with edible white ink. The capsule of the present invention may be prepared by using one gravure roll for the imprinting for the capsule cap and body if single color print is preferred.

In addition to the above-mentioned components, plasticizers; opacifying agents; or flavoring agents can also be added to the capsule, as required.

Any plasticizers may be used in capsules without limitation insofar as they can be used for medical drugs or food products. For example, dioctyl adipate, polyester adipate, epoxidated soybean oil, epoxy hexahydro phthalic acid diester, kaolin, triethyl citrate, glycerol, glycerol fatty acid ester, sesame oil, a polydimethylsiloxane-silicon dioxide mixture, D-sorbitol, medium chain fatty acid triglyceride, sugar alcohol solution originated corn starch, triacetin, concentrated glycerin, castor oil, phytosterol, diethyl phthalate, dioctyl phthalate, dibutyl phthalate, butyl phthalyl butyl glycolate, propylene glycol, polyoxyethylene (105) polyoxypropylene (5) glycol, polysorbate 80, macrogol 1500, macrogol 400, macrogol 4000, macrogol 600, macrogol 6000, isopropyl myristate, cotton seed oil-soybean oil mixture, glyceryl monostearate, isopropyl linolate, can be used as plasticizers.

Other ingredients in the capsule may include plasticizers such as glycerin and/or sorbitol to decrease the capsule's hardness, preservatives, disintegrants, lubricants and surface treatments. Specific ingredients or additives may include glycerine, calcium hydroxide, stearic acid, hydroxybutylanisol, estearic acid, cottonseed oil, vaseline oil, paraffin, monoglyceride citrate, potassium chloride, carageenan and antifoam including dimethypolysiloxane, sorbitan, and fatty acid ester.

Still other ingredients included in the capsule may include butyl alcohol, calcium hydroxide, citric acid, dehydrated alcohol, edetate calcium disodium, polyethylene glycol, polysorbate 80, purified water, shellac, sorbitan monooleate, sorbitan monostearate, sorbitan trioleate, monooleate sodium propionate, dimethicone, and fluid soybean lechithin.

The capsule of the present invention may include a flavoring agent such as an oil soluble flavoring agent. As used herein, the term "oil soluble flavoring agent" refers to any agent that provides an appealing flavor and whose solubility in water is from very slightly soluble to insoluble. In a particular embodiment, the agent is insoluble in water. In general, when an oil soluble flavoring agent of the invention is mixed with water, two phases are formed, an oil phase and a water phase, with substantially all of the oil soluble flavoring agent being in the oil phase.

Flavoring agents suitable for use in the present invention are well known in the art and include, but are not limited to, synthetic flavor oils, flavoring aromatics, oils, oleo resins and extracts derived from plants, leaves, flowers, fruits, and combinations thereof. These flavoring agents are generally liquids but can also be used as spray dried solids, powdered solids and the like. Suitable flavoring agents include, but are not limited to, spearmint oil, cinnamon oil, oil of wintergreen (methylsalicylate), peppermint oils, clove oil, bay oil, anise oil, eucalyptus oil, thyme oil, cedar leaf oil, oil of nutmeg, oil of sage, oil of bitter almonds, peanut butter flavor, chocolate flavor, rum flavor, cassia oil, cinnamon mint flavor, corn mint oil, cardamom flavor, ginger flavor, cola flavor, cherry cola flavor, and the like. Generally any flavoring agent such as those described in Chemicals Used in Food Processing, pub 1274 by the National Academy of Sciences, pages 63-258 may be used.

The flavoring agents may provide the composition with any appealing flavor, for example, that serves to mask an undesirable or unpleasant flavor or odor of the composition. In certain embodiments, the oil soluble flavoring agents may provide the composition with grape, apple, cinnamon, berry, strawberry, orange, cherry, lemon, lime, raspberry, peach, grapefruit, mango, guava, mint, chocolate, coca, vanilla, lemon, nut, almond, coconut, blueberry, blackberry, banana, pineapple, spearmint, wintergreen, peppermint, clove, bay, anise, eucalyptus, thyme, nutmeg, sage, bitter almonds, cinnamon mint, corn mint, cardamom, ginger, cola, rum, peanut butter and/or chocolate flavors. In other embodiments, blends of these flavors may be utilized.

The flavoring agents should be present in an amount sufficient to provide a distinct flavor perception on the part of the patient. In a particular embodiment, the flavoring agent should be present in an amount sufficient to mask an otherwise undesirable or unpleasant flavor of the capsule composition, for example, that of the active agent or of the gelatin forming the shell or incorporated into the fill. In another embodiment, the oil soluble flavoring agent is present in an amount sufficient to provide a sustained flavor perception on the part of the patient. For example, the flavor should be present in an amount sufficient to mask the undesirable or unpleasant flavor of the composition during the period that the composition is retained in the mouth. In one embodiment, the capsule includes at least about 0.01 wt % to about 25 wt %, or from 0.01 wt % to about 15 wt %, or from about 0.4 wt % and about 10 wt %, from about 1 wt % to about 8 wt %, of oil flavoring agent.

The present invention thus provides a capsule, especially a hard capsule, totally or partially comprising the above-mentioned mixture of colorants. The capsule of the present invention may be manufactured using a common immersion method, specifically as follows. A capsule-forming pin is dipped in a film-forming aqueous solution (hereinafter referred to as "capsule base solution" or "base solution") containing the foregoing ingredients. After the pin is pulled out of the solution, the layer of the base solution formed around the outer dimension of the capsule-forming pin is cooled to be gelatinized. Note that the contents of ingredients in the capsule base solution are adjustable by appropriately changing the proportions of the ingredients in the film-forming aqueous solution.

The water content of the water in the capsule base solution is not limited; however, the viscosity of the capsule base solution is generally 100 to 20,000 m Pas, preferably 300 to 10,000 m Pas, and further preferably 1,000 to 5,000 m Pas under the temperature (temperature of immersion liquid) in the immersion process for the capsule-forming pin (from 30 to 80° C., or from 40 to 60° C.).

The method for preparing the capsule base solution (immersion liquid) is not particularly limited. In one exemplary method, the water-soluble compound, HPMC, is dispersed in purified water heated to about 70 to about 80° C. in which a gelling agent is dissolved as necessary. The dispersion is then cooled to a desired temperature to obtain the target immersion liquid (generally from about 35 to about 60° C., or from about 40 to about 60° C.). The resulting jellylike liquid is mixed evenly with an aqueous solution. In another exemplary method, a water-soluble compound is dispersed in water heated to about 70 to about 80° C., and the solution is cooled to dissolve the water-soluble compound. After that, a gelling agent is dissolved in the solution as necessary. The resulting solution is heated again to about 30 to about 50° C., and mixed with an aqueous solution. The temperature of the aqueous solution is adjusted to obtain the target immersion liquid.

The capsule of the present invention may be produced by first dipping the capsule-forming pin in the capsule base solution (immersion liquid), then pulling the capsule-forming pin out of the capsule base solution, after which the layer of the base solution formed around the outer dimension of the capsule-forming pin is cooled to be gelatinized. Thereafter, the film is dried at about 20 to about 80° C. The capsule of the present invention may be manufactured through the following steps.

(1) Step of dipping a capsule-forming pin in a capsule base solution (immersion liquid) containing a water-soluble compound, (and a gelatinizer and gelling agent as necessary) (dipping step).

(2) Step of pulling the capsule-forming pin out of the capsule base solution, and gelatinizing the layer of the base solution formed around the outer dimension of the capsule-forming pin (gelatinization step).

(3) Step of drying the capsule base formed as a film layer on the outer portion of the capsule-forming pin (drying step).

(4) Step of removing the dry capsule base from the capsule-forming pin (removal step).

The following heating process (5) may be performed after the gelatinization step (2), before or during the drying process (3), or after the removal step (4).

(5) Step of heating the capsule base at about 50 to about 150° C. (heating process).

When a capsule base solution (immersion liquid) not containing a gelling agent such as carrageenan is used, step (2) can be performed by using a capsule-forming pin heated to about 60° C. or higher (thermal gelatinization), which relies on the fact that the water-soluble cellulose derivative is gelatinized at a temperature equal to or more than about 60° C. Specifically, the thermal gelatinization is performed as follows. A capsule-forming pin heated to an appropriate temperature according to the liquid temperature, for example, from about 60 to about 150° C., or from about 60 to about 120° C., or from about 70 to about 90° C., is dipped in a capsule base solution (immersion liquid) whose temperature is kept constant at about 35 to about 50° C., or from about 35 to about 45° C. Then, in gelatinization step (2), the capsule-forming pin is pulled out of the capsule base solution (immersion liquid), so that the capsule base solution formed around the outer dimension of the capsule-forming pin is gelatinized.

Meanwhile, when a capsule base solution (immersion liquid) containing a gelling agent, step (2) can be performed by adjusting the temperature in the vicinity of the capsule manufacturing apparatus to generally not more than about 35° C., or not more than about 30° C., or not more than about room temperature, so as to cool the capsule base solution formed around the outer dimension of the capsule-forming pin (cooling gelatinization). This relies on the fact that the solution is gelatinized at a temperature of about 50° C. or lower. Specifically, the cooling gelatinization is performed as follows. In step (1), a capsule-forming pin heated to an appropriate temperature according to the liquid temperature, for example, from about 10 to about 30° C., or from about 13 to about 28° C., or from about 15 to about 25° C., is dipped in a capsule base solution (immersion liquid) whose temperature is kept constant at about 35 to about 50° C., or from about 40 to about 60° C. Then, in gelatinization step (2), the capsule-forming pin is pulled out of the capsule base solution (immersion liquid), so that the capsule base solution formed around the outer dimension of the capsule-forming pin is gelatinized.

The drying process (3) can be performed at room temperature, often by blowing air of room temperature. The removal step (4) is carried out by removing the dry capsule base, formed around the outer portion of the capsule-forming pin, from the capsule-forming pin.

The arbitrary heating process (5) can be performed after gelatinization step (2)—in other words, after the capsule base solution is gelatinized (solidified). Heating may be performed any time after gelatinization step (2), for example, before, after, or during the drying process (3), or after the removal process (4). However, heating is preferably performed as follows. After gelatinization step (2), the gel capsule base is subjected to the drying process under room temperature. When the gel capsule base is dried or half-dried, the capsule base is heated. The heating temperature is not particularly limited; however, it preferably ranges from about 60 to about 100° C. or from about 60 to about 80° C. Generally, the heating can be performed by sending air of about 50 to about 150° C.

The capsule base thus prepared is cut to a predetermined length, and becomes available as a capsule body and cap set, or as separate parts.

The capsule of the present invention may include an active biological ingredient selected from nourishment tonics, antipyretics/analgesics/anti-inflammatory drugs, psychotropic drugs, anti-anxiety drugs, antidepressant drugs, hypnotic/sedative drugs, antispasmodic drugs, drugs acting on the central nervous system, cerebral metabolism improvers, cerebral circulation improvers, antiepileptic drugs, sympathetic nerve stimulants, digestives, antacids, antiulcer drugs, antitussive/expectorant drugs, antiemetic drugs, respiration promoters, bronchodilators, antiallergic drugs, drugs for dentistry and oral cavity, antihistamic drugs, cardiotonic drugs, antiarrhythmic drugs, diuretic drugs, antihypertensive drugs, vasoconstrictors, coronary vasodilators, peripheral vasodilators, antihyperlipidemic drugs, cholagogues, antibiotics, chemotherapeutic drugs, antidiabetic drugs; antiosteoporotic drugs, antirheumatic drugs, skeletal muscle relaxants, spasmolytic drugs, hormone preparations, alkaloid narcotics, sulfa drugs, anti-gout drugs, anticoagulant drugs, antineoplastic drugs, growth hormones, human growth hormones, recombinant human growth hormones, bovine growth hormones, porcine growth hormones, growth hormone releasing hormones, growth hormone releasing factor; interferons, .alpha.-interferon, .beta.-interferon, .gamma.-interferon; interleukin, interleukin-1, interleukin-2; insulin porcine insulin, bovine insulin, human insulin, human recombinant insulin, insulin-like growth factor, insulin-like growth factor-1; heparin unfractionated heparin, heparinoids, dermatans, chondroitins, low molecular weight heparin, very low molecular weight heparin, ultra low molecular weight heparin; calcitonin salmon calcitonin, eel calcitonin, human calcitonin; erythropoietin; atrial naturetic factor; antigens; monoclonal antibodies; somatostatin; protease inhibitors; adrenocorticotropin; gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium; sodium chromoglycate; disodium chromoglycate; vancomycin; desferrioxamine; parathyroid hormone; fragments of parathyroid hormone; antimicrobials; anti-fungal agents, and the like. Such active biological ingredients are not particularly limited, and a wide variety of known ones can be used.

When the capsule is filled with a food, examples of such foods include, but are not limited to, functional ingredients such as docosahexaenoic acid, eicosapentaenoic acid, .alpha.-lipoic acid, royal jelly, isoflavone, agaricus, acerola, aloe, aloe vera, turmeric, L-carnitine, oligosaccharide, cacao, catechin, capsaicin, chamomile, agar, tocopherol, linolenic acid, xylitol, chitosan, GABA, citric acid, chlorella, glucosamine, ginseng, coenzyme Q10, brown sugar, collagen, chondroitin, bracket fungus, squalene, stevia, ceramide, taurine, saponin, lecithin, dextrin, *Houttuynia cordata*, niacin, *Bacillus natto*, bittern, lactic acid bacteria, saw palmetto, honey, *Coix lacrymajobi* var. ma-yuen, ume extract, pantothenic acid, hyaluronic acid, vitamin A, vitamin K, vitamin C, vitamin D, vitamin B1, vitamin B2, vitamin B6, vitamin B12, quercetin, protein, propolis, mulukhiya, folic acid, lycopene, linoleic acid, rutin, and *Ganoderma lucidum*.

The filling of the contents in the hard capsule may be performed by using a per se known capsule-filling machine, such as a fully automatic capsule-filling machine (model name: "LIQFIL super 80/150", product of Qualicaps Co., Ltd.), and a capsule-filing and sealing machine (model name: LIQFIL super FS, product of Qualicaps Co., Ltd.), etc.

Pullulan, hemicellulose, corn starch, and carboxymethyl cellulose are widely used as additives for foods, drugs, cosmetics, etc., and are commercially available. Hemicellulose is preferably a soybean-derived hemicellulose. "Hemilose", a product of Fuji Oil Co., Ltd., is particularly preferable. Water-soluble salts thereof may be any salt that dissolves in water. Examples thereof include alkali metal salts such as sodium salts and potassium salts. In general, the hard capsule can be produced by an injection molding method or a dipping method. The dipping method is a capsule manufacturing method that makes: use of the gelatin of the hard capsule film-forming base material (hard capsule-preparation liquid) by a temperature difference. If the base material has no gelling capability, a gelling agent is added.

Sealing of the hard capsules, if necessary, can be conducted by use of a per se known capsule filling and sealing machine, such as the above-mentioned capsule filling and sealing machine (model name: HICAPSEAL 40/100, product of Qualicaps Co., Ltd.). These machines are fully automatic capsule sealing machines, which perform the banding of two-part capsules.

EXAMPLES AND COLOR EXTRACTS

In Example 1 and each of the extract colors the color space L, a, and b were measured in accordance to the Lab Color Test.

Example 1

The capsule of the present invention was prepared as follows. The following colorant amounts were added to about 1 L of a 35% gelatin solution in water:

10 mL of a 100 mg/mL solution of FD&C Blue No 1 in water;
10 mL of a 15 mg/mL solution of FD&C Blue No 2 in water;
5 mL of a 40 mg/mL solution of D&C Red 33 in water;
10 mL of a 40 mg/mL solution of FD&C Yellow No 6 in water;
10 mL of a 98 mg/mL solution of FD&C Red No 3 in water;
10 mL of a 100 mg/mL suspension of Iron Oxide Black in water;
10 mL of a 300 mg/mL suspension of Iron Oxide Red in water;
10 mL of a 150 mg/mL suspension of Iron Oxide Yellow in water;
25 mL of a 326 mg/mL suspension of Titanium Dioxide in water;
10 mL of a 100 mg/mL solution of FD&C Yellow No 5 in water;
10 mL of a 40 mg/mL solution of D&C Yellow No 10 in water;
10 mL of a 150 mg/mL solution of FD&C Red No 40 in water;
5 mL of a 100 mg/mL solution of D&C Red No 22 in water;
7 mL of a 100 mg/mL solution of D&C Red No 28 in water; and
5 mL of a 50 mg/mL solution of FD&C Green No 3 in water.

The sample was mixed by hand using a spatula until homogenous. This resulted in a colored gelatin solution suitable for the manufacture of hard gelatin capsules. An about 60 mL aliquot of this colored gelatin solution was poured in to a 100 mm×15 mm petri dish. The sample dispersion across the bottom of the dish along with the layer thickness of the sample in the dish gave an appropriate presentation for measurement using the Hunter Lab LABSCAN® XE spectrocolorimeter. Five readings for the spectrocolorimeter were obtained for the presented surface. The spectrocolorimeter software averaged these readings to report values of L=14.97, a=6.49, b=−0.54 for the colored gelatin solution.

Example 2

The capsule of the present invention was imprinted using edible ink which was black in appearance (hereinafter referred to as "black edible ink") for the cap portion of the capsule and edible ink which was white in appearance (hereinafter referred to as "white ink") for the body portion of the capsule. The black edible ink used in this example was black ink SW-9008 available from TEK Products & Services, Inc. of Reading Pa. and black ink S-1-17823 available from Colorcon of West Point, Pa. The white edible ink used in this example was white ink SB-0007P available from TEK Products & Services, Inc. of Reading, Pa. and white ink S-1-7085 available from Colorcon of West Point, Pa.

To assure proper homogeneity of the ink, each ink container was mixed using a mechanical shaker immediately prior to use. Solvents may also be added to the inks at time of use to adjust ink viscosity and drying time. Adjustments to these parameters may be required to achieve the appropriate quality of imprinting and depend greatly on the design to be imprinted on the capsules. The solvents utilized to make these adjustments are limited to those present in the original ink formulation as supplied by the manufacturer. Preferred solvents include butyl alcohol, ethyl alcohol, and propylene glycol.

Color Extracts

Color Extract A—The Blue-Green Extract Color was prepared by the addition of 10 mL of a 100 mg/mL solution of FD&C Blue No 1 in water and 9 mL of a 326 mg/mL suspension of Titanium Dioxide in water to about 1 L of a 35% gelatin solution in water. The sample was mixed by hand using a spatula until homogenous. This resulted in a colored gelatin solution suitable for the manufacture of hard gelatin capsules. An about 60 mL aliquot of this colored gelatin solution was poured in to a 100 mm×15 mm petri dish. The sample dispersion across the bottom of the dish along with the layer thickness of the sample in the dish gave an appropriate presentation for measurement using the Hunter Lab LABSCAN® XE spectrocolorimeter. Five readings for the spectrocolorimeter were obtained for the presented surface. The spectrocolorimeter software averaged these readings to report values of L=35.43, a=−16.89, b=−37.07 for the colored gelatin solution.

Color Extract B—The Orange Extract Color was prepared by the addition of 10 mL of a 40 mg/mL solution of FD&C Yellow No 6 in water and 9 mL of a 326 mg/mL suspension of Titanium Dioxide in water to about 1 L of a 35% gelatin solution in water. The sample was mixed by hand using a spatula until homogenous. This resulted in a colored gelatin solution suitable for the manufacture of hard gelatin capsules. An about 60 mL aliquot of this colored gelatin solution was poured in to a 100 mm×15 mm petri dish. The sample dispersion across the bottom of the dish along with the layer thickness of the sample in the dish gave an appropriate presentation for measurement using the Hunter Lab LABSCAN® XE spectrocolorimeter. Five readings for the spectrocolorimeter were obtained for the presented surface. The spectrocolorimeter software averaged these readings to report values of L=63.71, a=37.29, b=33.02 for the colored gelatin solution.

Color Extract C—The Dark Red Extract Color was prepared by the addition of 10 mL of a 150 mg/mL solution of FD&C Red No 40 in water and 9 mL of a 326 mg/mL suspension of Titanium Dioxide in water to about 1 L of a 35% gelatin solution in water. The sample was mixed by hand using a spatula until homogenous. This resulted in a colored gelatin solution suitable for the manufacture of hard gelatin capsules. An about 60 mL aliquot of this colored gelatin solution was poured in to a 100 mm×15 mm petri dish. The sample dispersion across the bottom of the dish along with the layer thickness of the sample in the dish gave an appropriate presentation for measurement using the Hunter Lab LABSCAN® XE spectrocolorimeter. Five readings for the spectrocolorimeter were obtained for the presented surface. The spectrocolorimeter software averaged these readings to report values of L=35.47, a=54.09, b=16.96 for the colored gelatin solution.

Color Extract D—The Lemon Yellow Extract Color was prepared by the addition of 10 mL of a 40 mg/mL solution of D&C Yellow No 10 in water and 9 mL of a 326 mg/mL suspension of Titanium Dioxide in water to about 1 L of a 35% gelatin solution in water. The sample was mixed by hand using a spatula until homogenous. This resulted in a colored gelatin solution suitable for the manufacture of hard gelatin capsules. An about 60 mL aliquot of this colored gelatin solution was poured in to a 100 mm×15 mm petri dish. The sample dispersion across the bottom of the dish along with the layer thickness of the sample in the dish gave an appropriate presentation for measurement using the Hunter Lab LAB-SCAN® XE spectrocolorimeter. Five readings for the spectrocolorimeter were obtained for the presented surface. The spectrocolorimeter software averaged these readings to report values of L=84.59, a=−10.57, b=40.99 for the colored gelatin solution.

Color Extract E—The Blue-Violet Extract Color was prepared by the addition of 10 mL of a 15 mg/mL solution of FD&C Blue No 2 in water and 9 mL of a 326 mg/mL suspension of Titanium Dioxide in water to about 1 L of a 35% gelatin solution in water. The sample was mixed by hand using a spatula until homogenous. This resulted in a colored gelatin solution suitable for the manufacture of hard gelatin capsules. An about 60 mL aliquot of this colored gelatin solution was poured in to a 100 mm×15 mm petri dish. The sample dispersion across the bottom of the dish along with the layer thickness of the sample in the dish gave an appropriate presentation for measurement using the Hunter Lab LAB-SCAN® XE spectrocolorimeter. Five readings for the spectrocolorimeter were obtained for the presented surface. The spectrocolorimeter software averaged these readings to report values of L=54.42, a=−14.14, b=−19.70 for the colored gelatin solution.

Color Extract F—The Red Extract Color was prepared by the addition of 5 mL of a 40 mg/mL solution of D&C Red No 33 in water and 9 mL of a 326 mg/mL suspension of Titanium Dioxide in water to about 1 L of a 35% gelatin solution in water. The sample was mixed by hand using a spatula until homogenous. This resulted in a colored gelatin solution suitable for the manufacture of hard gelatin capsules. An about 60 mL aliquot of this colored gelatin solution was poured in to a 100 mm×15 mm petri dish. The sample dispersion across the bottom of the dish along with the layer thickness of the sample in the dish gave an appropriate presentation for measurement using the Hunter Lab LABSCAN® XE spectrocolorimeter. Five readings for the spectrocolorimeter were obtained for the presented surface. The spectrocolorimeter software averaged these readings to report values of L=34.21, a=46.20, b=−4.48 for the colored gelatin solution.

Color Extract G—The Fluorescent Red Extract Color was prepared by the addition of 7 mL of a 100 mg/mL solution of D&C Red No 28 in water and 9 mL of a 326 mg/mL suspension of Titanium Dioxide in water to about 1 L of a 35% gelatin solution in water. The sample was mixed by hand using a spatula until homogenous. This resulted in a colored gelatin solution suitable for the manufacture of hard gelatin capsules. An about 60 mL aliquot of this colored gelatin solution was poured in to a 100 mm×15 mm petri dish. The sample dispersion across the bottom of the dish along with the layer thickness of the sample in the dish gave an appropriate presentation for measurement using the Hunter Lab LAB-SCAN® XE spectrocolorimeter. Five readings for the spectrocolorimeter were obtained for the presented surface. The spectrocolorimeter software averaged these readings to report values of L=55.75, a=74.47, b=8.10 for the colored gelatin solution.

Color Extract H—The Bright Red Extract Color was prepared by the addition of 10 mL of a 98 mg/mL solution of FD&C Red No 3 in water and 9 mL of a 326 mg/mL suspension of Titanium Dioxide in water to about 1 L of a 35% gelatin solution in water. The sample was mixed by hand using a spatula until homogenous. This resulted in a colored gelatin solution suitable for the manufacture of hard gelatin capsules. An about 60 mL aliquot of this colored gelatin solution was poured in to a 100 mm×15 mm petri dish. The sample dispersion across the bottom of the dish along with the layer thickness of the sample in the dish gave an appropriate presentation for measurement using the Hunter Lab LAB-SCAN® XE spectrocolorimeter. Five readings for the spectrocolorimeter were obtained for the presented surface. The spectrocolorimeter software averaged these readings to report values of L=50.88, a=66.89, b=7.75 for the colored gelatin solution.

Color Extract I—The Green Extract Color was prepared by the addition of 5 mL of a 50 mg/mL solution of FD&C Green No 3 in water and 9 mL of a 326 mg/mL suspension of Titanium Dioxide in water to about 1 L of a 35% gelatin solution in water. The sample was mixed by hand using a spatula until homogenous. This resulted in a colored gelatin solution suitable for the manufacture of hard gelatin capsules. An about 60 mL aliquot of this colored gelatin solution was poured in to a 100 mm×15 mm petri dish. The sample dispersion across the bottom of the dish along with the layer thickness of the sample in the dish gave an appropriate presentation for measurement using the Hunter Lab LABSCAN® XE spectrocolorimeter. Five readings for the spectrocolorimeter were obtained for the presented surface. The spectrocolorimeter software averaged these readings to report values of L=43.30, a=−30.54, b=−10.27 for the colored gelatin solution.

Color Extract J—The Pale Red Extract Color was prepared by the addition of 10 mL of a 300 mg/mL suspension of Iron Oxide Red in water and 9 mL of a 326 mg/mL suspension of Titanium Dioxide in water to about 1 L of a 35% gelatin solution in water. The sample was mixed by hand using a spatula until homogenous. This resulted in a colored gelatin solution suitable for the manufacture of hard gelatin capsules. An about 60 mL aliquot of this colored gelatin solution was poured in to a 100 mm×15 mm petri dish. The sample dispersion across the bottom of the dish along with the layer thickness of the sample in the dish gave an appropriate presentation for measurement using the Hunter Lab LABSCAN® XE spectrocolorimeter. Five readings for the spectrocolorimeter were obtained for the presented surface. The spectrocolorimeter software averaged these readings to report values of L=34.81, a=26.25, b=10.93 for the colored gelatin solution.

Color Extract K—The Pale Yellow Extract Color was prepared by the addition of 10 mL of a 150 mg/mL suspension of Iron Oxide Yellow in water and 9 mL of a 326 mg/mL suspension of Titanium Dioxide in water to about 1 L of a 35% gelatin solution in water. The sample was mixed by hand using a spatula until homogenous. This resulted in a colored gelatin solution suitable for the manufacture of hard gelatin capsules. An about 60 mL aliquot of this colored gelatin solution was poured in to a 100 mm×15 mm petri dish. The sample dispersion across the bottom of the dish along with the layer thickness of the sample in the dish gave an appropriate presentation for measurement using the Hunter Lab LAB-SCAN® XE spectrocolorimeter. Five readings for the spectrocolorimeter were obtained for the presented surface. The spectrocolorimeter software averaged these readings to report values of L=66.73, a=12.25, b=29.04 for the colored gelatin solution.

Color Extract L—The Grey Extract Color was prepared by the addition of 10 mL of a 100 mg/mL suspension of Iron Oxide Black in water and 9 mL of a 326 mg/mL suspension of Titanium Dioxide in water to about 1 L of a 35% gelatin solution in water. The sample was mixed by hand using a spatula until homogenous. This resulted in a colored gelatin solution suitable for the manufacture of hard gelatin capsules. An about 60 mL aliquot of this colored gelatin solution was poured in to a 100 mm×15 mm petri dish. The sample dispersion across the bottom of the dish along with the layer thickness of the sample in the dish gave an appropriate presentation for measurement using the Hunter Lab LABSCAN® XE spectrocolorimeter. Five readings for the spectrocolorimeter were obtained for the presented surface. The spectrocolorimeter software averaged these readings to report values of L=45.66, a=−0.87, b=−14.8 for the colored gelatin solution.

Color Extract M—The Deep Yellow Extract was prepared by the addition of 10 mL of a 100 mg/mL solution of FD&C Yellow No 5 in water to about 1 L of a 35% gelatin solution in water. The sample was mixed by hand using a spatula until homogenous. This resulted in a colored gelatin solution suitable for the manufacture of hard gelatin capsules. An about 60 mL aliquot of this colored gelatin solution was poured in to a 100 mm×15 mm petri dish. The sample dispersion across the bottom of the dish along with the layer thickness of the sample in the dish gave an appropriate presentation for measurement using the Hunter Lab LABSCAN® XE spectrocolorimeter. Five readings for the spectrocolorimeter were obtained for the presented surface. The spectrocolorimeter software averaged these readings to report values of L=78.60, a=1.71, b=45.92 for the colored gelatin solution.

Color Extract N—The Orange-Pink Extract Color was prepared by the addition of 5 mL of a 100 mg/mL solution of D&C Red No 22 in water and 9 mL of a 326 mg/mL suspension of Titanium Dioxide in water to about 1 L of a 35% gelatin solution in water. The sample was mixed by hand using a spatula until homogenous. This resulted in a colored gelatin solution suitable for the manufacture of hard gelatin capsules. An about 60 mL aliquot of this colored gelatin solution was poured in to a 100 mm×15 mm petri dish. The sample dispersion across the bottom of the dish along with the layer thickness of the sample in the dish gave an appropriate presentation for measurement using the Hunter Lab LABSCAN® XE spectrocolorimeter. Five readings for the spectrocolorimeter were obtained for the presented surface. The spectrocolorimeter software averaged these readings to report values of L=67.84, a=54.98, b=29.38 for the colored gelatin solution.

Color Extract O— The White Extract Color was prepared by the addition of 25 mL of a 326 mg/mL suspension of Titanium Dioxide in water to about 1 L of a 35% gelatin solution in water. The sample was mixed by hand using a spatula until homogenous. This resulted in a colored gelatin solution suitable for the manufacture of hard gelatin capsules. An about 60 mL aliquot of this colored gelatin solution was poured in to a 100 mm×15 mm petri dish. The sample dispersion across the bottom of the dish along with the layer thickness of the sample in the dish gave an appropriate presentation for measurement using the Hunter Lab LABSCAN® XE spectrocolorimeter. Five readings for the spectrocolorimeter were obtained for the presented surface. The spectrocolorimeter software averaged these readings to report values of L=89.90, a=0.11, b=8.95 for the colored gelatin solution.

The table below includes color measurements for the color values of the Color Solution of Example 1 and extracted colors to demonstrate the color range possible using the ingredients from this capsule

TABLE 3

| | Colorants | Hunter L | Hunter a | Hunter b |
|---|---|---|---|---|
| Ex. 1 | Mixture of Colorants | 14.97 | 6.49 | −0.54 |
| A | Blue-green extract color (B1 + $TiO_2$) | 35.43 | −16.89 | −37.07 |
| B | Orange extract color (Y6 + $TiO_2$) | 63.71 | 37.29 | 33.02 |
| C | Dark red extract color (R40 + $TiO_2$) | 35.47 | 54.09 | 16.96 |
| D | Lemon yellow extract color (Y10 + $TiO_2$) | 84.59 | −10.57 | 40.99 |
| E | Blue-violet extract color (B2 + $TiO_2$) | 54.42 | −14.14 | −19.70 |
| F | Red extract color (R33 + $TiO_2$) | 34.21 | 46.20 | −4.48 |
| G | Fluorescent Red extract color (R28 + $TiO_2$) | 55.75 | 74.47 | 8.10 |
| H | Bright Red extract color (R3 + $TiO_2$) | 50.88 | 66.89 | 7.75 |
| I | Green extract color (G3 + $TiO_2$) | 43.30 | −30.54 | −10.27 |
| J | Pale Red extract color (IOR + $TiO_2$) | 34.81 | 26.25 | 10.93 |
| K | Pale Yellow extract color (IOY + $TiO_2$) | 66.73 | 12.25 | 29.04 |
| L | Grey extract color (IOB + $TiO_2$) | 45.66 | −.087 | −1.48 |
| M | Deep Yellow extract color (Y5 + $TiO_2$) | 78.60 | 1.71 | 45.92 |
| N | White Extract Color ($TiO_2$) | 89.90 | 0.11 | 8.95 |
| O | Orange -Pink Extract Color (R22 + $TiO_2$) | 67.84 | 54.98 | 29.38 |

Notwithstanding that the numerical ranges and parameters setting forth the broad scope of the invention are approximations, the numerical values set forth in the specific examples are reported as precisely as possible. Other than in the operating examples, or where otherwise indicated, all numbers expressing quantities of ingredients, reaction conditions, and so forth used in the specification and claims are to be understood as being modified in all instances by the term "about." Any numerical value, however, inherently contain certain errors necessarily resulting from the standard deviation found in their respective testing measurements.

What is claimed is:

1. A capsule comprising:
 a) a water-soluble compound suitable for the capsule,
 b) a mixture of colorant agents comprising up to about 0.35 wt % of iron oxide yellow, up to about 0.24 wt % of iron oxide black, up to about 0.70 wt % of iron oxide red, up to about 1.92 wt % of titanium dioxide, up to about 0.23 wt % of FD&C Blue No 1, up to about 0.04 wt % of FD&C Blue No 2, up to about 0.09 wt % of FD&C Yellow No 6, up to about 0.23 wt % of FD&C Yellow No 5, up to about 0.35 wt % of FD&C Red No 40, up to about 0.23 wt % of FD&C Red No 3, up to about 0.12 wt % of D&C Red No 22, up to about 0.05 wt % of D&C Red No 33, up to about 0.16 wt % of D&C Red No 28, up to about 0.06 wt % of FD&C Green No 3, and up to about 0.09 wt % of D&C Yellow No 10; and
 c) an edible ink imprinted on the capsule.

2. The capsule according to claim 1 wherein the color of the capsule may be in the range of 15<L<90; −30<a<+75; −37<b<+46 as measured in accordance with the Lab color space.

3. The capsule according to claim 1 wherein the water-soluble compound is selected from gelatin or cellulose compound and the gelatin is substituted with hydroxypropyl methylcellulose.

4. The capsule according to claim 1 further comprising a gelling agent.

5. The capsule according to claim 4 wherein the gelling agent is at least one member selected from carrageenan, pectin, xanthan gum, locust bean gum, tamarind seed polysaccharide, curdlan, gelatin, fur selenium, agar, and gellan gum.

6. The capsule according to claim 4 wherein the gelling agent is carrageenan.

7. The capsule according to claim 1 wherein the capsule is imprinted with at least two edible inks.

8. The capsule according to claim 1 contains a filling.

9. The capsule according to claim 8, wherein the filling is food, medicine, cosmetics, agrichemicals, feed or an active biological ingredient.

10. The capsule according to claim 8 wherein the filling is selected from the group consisting of: nourishment tonics, antipyretics/analgesics/anti-inflammatory drugs, psychotropic drugs, anti-anxiety drugs, antidepressant drugs, hypnotic/sedative drugs, antispasmodic drugs, drugs acting on the central nervous system, cerebral metabolism improvers, cerebral circulation improvers, antiepileptic drugs, sympathetic nerve stimulants, digestives, antacids, antiulcer drugs, antitussive/expectorant drugs, antiemetic drugs, respiration promoters, bronchodilators, antiallergic drugs, drugs for dentistry and oral cavity, antihistamic drugs, cardiotonic drugs, antiarrhythmic drugs, diuretic drugs, antihypertensive drugs, vasoconstrictors, coronary vasodilators, peripheral vasodilators, antihyperlipidemic drugs, cholagogues, antibiotics, chemotherapeutic drugs, antidiabetic drugs; antiosteoporotic drugs, antirheumatic drugs, skeletal muscle relaxants, spasmolytic drugs, hormone preparations, alkaloid narcotics, sulfa drugs, anti-gout drugs, anticoagulant drugs, antineoplastic drugs, growth hormones, human growth hormones, recombinant human growth hormones, bovine growth hormones, porcine growth hormones, growth hormone releasing hormones, growth hormone releasing factor;

interferons, alpha-interferon, beta-interferon, gamma-interferon; interleukin, interleukin-1, interleukin-2; insulin porcine insulin, bovine insulin, human insulin, human recombinant insulin, insulin-like growth factor, insulin-like growth factor-1; heparin unfractionated heparin, heparinoids, dermatans, chondroitins, low molecular weight heparin, very low molecular weight heparin, ultra low molecular weight heparin; calcitonin salmon calcitonin, eel calcitonin, human calcitonin; erythropoietin; atrial naturetic factor; antigens; monoclonal antibodies; somatostatin; protease inhibitors; adrenocorticotropin; gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium; sodium chromoglycate; disodium chromoglycate; vancomycin; desferrioxamine; parathyroid hormone; fragments of parathyroid hormone; antimicrobials; anti-fungal agents; vitamins; and any combination thereof.

11. A capsule comprising:
a) a water-soluble compound suitable for the capsule,
b) a mixture of colorant agents comprising colors up to about 0.24 wt % of E172(i), up to about 0.70 wt % of E172(ii), up to about 0.35 wt % of E172(iii), up to about 1.92 wt % of E171, up to about 0.23 wt % of E133, up to about 0.09 wt % of E110, up to about 0.35 wt % of E129; E131; E123, E122, E150, E120, E124, E140, E129, up to about 0.23 wt % of E127, up to about 0.04 wt % of E132, up to about 0.23 wt % of E102; up to about 0.06 wt % of E143; and E151, and c) an edible ink imprinted on the capsule.

12. The capsule according to claim 11 wherein the color of the capsule may be in the range of 15<L<90; −30<a<+75; −37<b<+46 as measured in accordance with the Lab color space.

13. The capsule according to claim 11 wherein the water-soluble compound is selected from gelatin or cellulose compound and the gelatin is substituted with hydroxypropyl methylcellulose.

14. The capsule according to claim 11 further comprising a gelling agent.

15. The capsule according to claim 14 wherein the gelling agent is at least one member selected from carrageenan, pectin, xanthan gum, locust bean gum, tamarind seed polysaccharide, curdlan, gelatin, fur selenium, agar, and gellan gum.

16. The capsule according to claim 14 wherein the gelling agent is carrageenan.

17. The capsule according to claim 11 wherein the capsule is imprinted with at least two edible inks.

18. The capsule according to claim 11 contains a filling.

19. The capsule according to claim 18, wherein the filling is food, medicine, cosmetics, agrichemicals, feed or an active biological ingredient.

20. The capsule according to claim 18 wherein the filling is selected from the group consisting of: nourishment tonics, antipyretics/analgesics/anti-inflammatory drugs, psychotropic drugs, anti-anxiety drugs, antidepressant drugs, hypnotic/sedative drugs, antispasmodic drugs, drugs acting on the central nervous system, cerebral metabolism improvers, cerebral circulation improvers, antiepileptic drugs, sympathetic nerve stimulants, digestives, antacids, antiulcer drugs, antitussive/expectorant drugs, antiemetic drugs, respiration promoters, bronchodilators, antiallergic drugs, drugs for dentistry and oral cavity, antihistamic drugs, cardiotonic drugs, antiarrhythmic drugs, diuretic drugs, antihypertensive drugs, vasoconstrictors, coronary vasodilators, peripheral vasodilators, antihyperlipidemic drugs, cholagogues, antibiotics, chemotherapeutic drugs, antidiabetic drugs; antiosteoporotic drugs, antirheumatic drugs, skeletal muscle relaxants, spasmolytic drugs, hormone preparations, alkaloid narcotics, sulfa drugs, anti-gout drugs, anticoagulant drugs, antineoplastic drugs, growth hormones, human growth hormones, recombinant human growth hormones, bovine growth hormones, porcine growth hormones, growth hormone releasing hormones, growth hormone releasing factor; interferons, alpha-interferon, beta-interferon, gamma-interferon; interleukin, interleukin-1, interleukin-2; insulin porcine insulin, bovine insulin, human insulin, human recombinant insulin, insulin-like growth factor, insulin-like growth factor-1; heparin unfractionated heparin, heparinoids, dermatans, chondroitins, low molecular weight heparin, very low molecular weight heparin, ultra low molecular weight heparin; calcitonin salmon calcitonin, eel calcitonin, human calcitonin; erythropoietin; atrial naturetic factor; antigens; monoclonal antibodies; somatostatin; protease inhibitors; adrenocorticotropin; gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium; sodium chromoglycate; disodium chromoglycate; vancomycin; desferrioxamine; parathyroid hormone; fragments of parathyroid hormone; antimicrobials; anti-fungal agents; vitamins; and any combination thereof.

\* \* \* \* \*